United States Patent [19]

Bohanon et al.

[11] Patent Number: 5,556,643

[45] Date of Patent: Sep. 17, 1996

[54] ANTICOAGULANT COMPOSITIONS

[75] Inventors: Leo F. Bohanon, Oconomowoc; Robert A. Adams, Brookfield; Daniel R. Kruszka, Janesville, all of Wis.

[73] Assignee: Hydrite Chemical Co., Brookfield, Wis.

[21] Appl. No.: 171,993

[22] Filed: Dec. 22, 1993

[51] Int. Cl.⁶ .......................... A61K 33/42; A61K 33/08; A61K 31/19

[52] U.S. Cl. .......................... 424/602; 424/603; 424/688; 424/690; 424/692; 424/693; 514/557; 514/574; 514/822

[58] Field of Search .................................... 514/557, 822, 514/574; 424/688, 690, 692, 693, 602, 603

[56] References Cited

U.S. PATENT DOCUMENTS 3,615,827  10/1971  Murphy ................................. 252/127
3,653,499   4/1972  Richter ................................. 206/47

OTHER PUBLICATIONS

Remington's Pharmaceutical Sciences, 17th Edition, Mack Printing Company, Easton, PA 1985, pp. 828, 829.
E. B. Donnelly et al, "Studies on Slaughter Animal Blood Plasma," Ir. J. Fd Sci. Technology, 2:31–38, 1978.
A. K. W. Tong, et al., "Blood Composition of Different Beef Breed Types," Can. J. Anim. Sci. 66: 915–924 (Dec. 1986).
FMC Corporation brochure (Sep. 30, 1988) "Technical Data Sodium Polyphosphates, Glassy Sodium Hexametaphosphate Technical Grade."The Merck Index, 10th Ed. (1983) abstract Nos. 2297 and 8509.

*Primary Examiner*—Kevin E. Weddington
*Attorney, Agent, or Firm*—Quarles & Brady

[57] ABSTRACT

An anticoagulant for blood contains sodium hydroxide, citric acid and sodium hexametaphosphate. A method of preventing the clotting of blood using the anticoagulant also is disclosed.

4 Claims, No Drawings

ANTICOAGULANT COMPOSITIONS

FIELD OF THE INVENTION

The present invention generally relates to the treatment of blood. More particularly, it relates to anticoagulant compositions and methods for treating blood.

BACKGROUND OF THE INVENTION

High quality animal blood is a source of valuable protein additives for use in the food industry. Powdered red blood cells (RBC) from pigs and cattle have been used to make dark breads in Europe and in pet foods. In addition, powdered plasma protein because of its functional properties has been used as a protein additive in meat and confectionery products.

At the present time, the blood which is used to prepare protein additives is collected in slaughterhouses, a solution of sodium citrate is added to the blood as an anticoagulant, and, the blood is separated by centrifugation or other means into its RBC and plasma protein fractions. The resulting fractions are concentrated or purified, if desired, to food grade standards by use of reverse osmosis or other conventional protein purification techniques.

The use of sodium citrate solutions as anticoagulants is not without disadvantages. One disadvantage is that the concentrations of sodium citrate which must be used are relatively high (6 to 8% by weight) and result in significant ash. Another disadvantage is that the separation of blood which has been treated with a conventional sodium citrate solution, into its protein fractions, tends to foul the separation and purification equipment.

It obviously would be advantageous to have better anticoagulants and methods for treating blood than those presently used.

BRIEF SUMMARY OF THE INVENTION

It is an object of the present invention to disclose novel anticoagulant compositions which do not possess the disadvantages of the presently used sodium citrate solutions.

It is a further object to disclose methods of using the novel anticoagulants to treat blood.

The anticoagulants of the present invention are dry mixes or aqueous preparations which contain effective amounts of alkaline metal ions, polycarboxylic acid ions and polyphosphate ions to prevent the clotting of the blood to which they are added.

An aqueous anticoagulant preparation can be prepared by dissolving about 0.5% to about 33% by weight of an alkaline metal hydroxide, about 0.5% to about 25% by weight of a polycarboxylic acid and about 0.5% to about 50% by weight of an alkaline polyphosphate in water.

In the method of the present invention, a clotting preventing amount of the anticoagulant is added to the blood so that the blood contains about 0.01 to about 0.05% alkaline metal (Na+) ions, about 0.01 to about 0.03% of polycarboxylic acid (citrate) ions and about 0.05 to about 0.20% of polyphosphate (hexametaphosphate) ions, the protein fractions are then separated and, if desired, purified.

The anticoagulants of the present invention are just as effective as anticoagulants as sodium citrate. In addition, they also are less expensive and less susceptible to microbial growth than the conventional sodium citrate anticoagulants.

From the description which follows, it will be readily apparent to those skilled in the art that the above and additional objects are obtained and additional advantages can be achieved by the practice of the present invention.

DESCRIPTION OF THE PREFERRED EMBODIMENT

In the preferred practice of the present invention the anticoagulant is an aqueous preparation containing the following ingredients by weight:

| | |
|---|---|
| Sodium Hexametaphosphate | about 25% |
| Citric Acid | about 3% |
| Sodium Hydroxide | about 4% |
| Water | about 68% |

It has a pH of 6.0 to 7.0 and it can be added to the blood as is (e.g. 1 part to 100 parts of blood) or prediluted (e.g. 1 part anticoagulant to 9 parts water) and then added to the blood.

The anticoagulant may also take the form of a dry mixture containing soluble sources of ions, such as a mixture of sodium citrate and sodium hexametaphosphate.

In one preferred method of the present invention, an effective amount of the anticoagulant is added to the blood so that the blood contains about 2% to about 6% (preferably 3% to about 4%) by weight of the anticoagulant on a solids basis. It is especially preferred that the blood contain between about 0.01 to about 0.02% of citrate ions, about 0.02 to about 0.04% of sodium ions and about 0.08 to about 0.16% of polyphosphate ions contributed by the anticoagulant.

In other embodiments of the method of the present invention, the anticoagulant is formed in situ in the blood by adding citric acid, sodium hydroxide and sodium hexametaphosphate to the blood or by adding a dry mixture of sodium citrate and sodium hexametaphosphate to the blood.

In place of the preferred citric acid, it may be desired in some instances to use as the polycarboxylic acid an acid selected from tartaric acid, gluconic acid, glucoheptonic acid and succinic acid.

In place of the sodium hydroxide it is possible to use potassium hydroxide or ammonium hydroxide to supply the alkaline metal ions. For convenience sodium ions, potassium ions, ammonium ions and other ions which function in a similar manner as sodium ions are referred to herein as "alkaline metal ions".

The preferred polyphosphate for use in the present invention is sodium hexametaphosphate $[(NaPO_3)_{13}]$. However, other alkaline hexametaphosphate salts might be used, as well as, glassy alkaline phosphate salts, such as sodaphos $[(NaPO_3)_6]$, glass H $[(NaPO_3)_{21}]$, sodium tripolyphosphate, tetrapotassium pyrophosphate, and potassium tripolyphosphate.

The practice of the invention is illustrated by the following examples:

EXAMPLE 1

An anticoagulant was made having the following composition:

|  | Percent by weight |
| --- | --- |
| Sodium Hexametaphosphate | 25.00 |
| Citric Acid | 3.27 |
| Sodium Hydroxide solution (50%) | 4.08 |
| Water | 67.65 |

In preparing the anticoagulant, the sodium hydroxide solution was first added to about one-half the water; the citric acid and sodium hexametaphosphate were added to the other half of the water; and, the two mixtures were combined with stirring to form a uniform aqueous preparation.

EXAMPLE 2

To demonstrate the usefulness of the anticoagulant of Example 1, 1 part of the anticoagulant was prediluted with 9 parts water and added to porcine blood. After 30 minutes the blood which had not clotted was separated into a RBC protein fraction and a plasma protein fraction by use of a (Alfa Laval) separator. The separated fractions were then purified by subjecting them to reverse osmosis using a polysulfone membrane in a commercially available reverse osmosis unit (Sepra Tec).

The dry purified fractions of RBC protein and plasma protein which were obtained were of superior quality. In addition, it was noted that the separator was not as difficult to clean as when a conventional sodium citrate solution was used as the anticoagulant. It also was observed that it was possible to save energy by using less pressure for the reverse osmosis concentration than could be used when conventional sodium citrate solution was used as the anticoagulant.

It will be readily apparent to those skilled in the art that a number of changes and modifications can be made without departing from the spirit and scope of the invention. Therefore, it is intended that the invention be only limited by the claims.

We claim:

1. An anticoagulant composition for animal blood consisting essentially of alkaline metal ions, polycarboxylic acid ions, and polyphosphate selected from the group consisting of sodium hexametaphosphate, sodaphos, glass H [(NAP03)21], sodium tripolyphosphate, tetrapotassium pyrophosphate and potassium tripolyphosphate.

2. An anticoagulant composition of claim 1 in which the polyphosphate is sodium hexametaphosphate.

3. An anticoagulant composition for animal blood consisting essentially of sodium citrate and sodium hexametaphosphate in amounts effective to act as an anticoagulant.

4. An anticoagulant composition for animal blood consisting essentially of:

(a) about 25% of an alkaline metal hexametaphosphate salt;

(b) about 3% of citric acid;

(c) about 4% of an alkaline metal hydroxide; and (d) about 68% of water.

* * * * *

UNITED STATES PATENT AND TRADEMARK OFFICE
CERTIFICATE OF CORRECTION

Patent No.    : 5,556,643
Dated         : September 17, 1997
Inventor(s)   : Leo F. Bohanon
                Robert A. Adams
                Daniel R. Kruszka It is certified that error appears in the above-identified patent and that said Letters Patent is hereby corrected as shown below:

Column 4, line 16 (Claim 1, line 5)

"[(NAP03)21]" should be --[$(NaPO_3)_{21}$]--.

Signed and Sealed this

Twenty-fourth Day of December, 1996

Attest:

BRUCE LEHMAN

*Attesting Officer*    *Commissioner of Patents and Trademarks*